United States Patent
Baldi

(10) Patent No.: US 11,564,960 B2
(45) Date of Patent: Jan. 31, 2023

(54) PROCESS FOR MAKING A WATER SOLUBLE, FULL SPECTRUM HEMP OIL

(71) Applicant: NORTHEAST KIND ASSETS, LLC, Eliot, ME (US)

(72) Inventor: Gregory S. Baldi, Kittery, ME (US)

(73) Assignee: NORTHEAST KIND ASSETS, LLC, Eliot, ME (US)

(*) Notice: Subject to any disclaimer, the term of this patent is extended or adjusted under 35 U.S.C. 154(b) by 142 days.

(21) Appl. No.: 17/195,750

(22) Filed: Mar. 9, 2021

(65) Prior Publication Data

US 2021/0275619 A1    Sep. 9, 2021

Related U.S. Application Data

(60) Provisional application No. 62/986,901, filed on Mar. 9, 2020.

(51) Int. Cl.

| | |
|---|---|
| A61K 36/185 | (2006.01) |
| A61K 9/107 | (2006.01) |
| A23L 33/105 | (2016.01) |
| A23L 3/46 | (2006.01) |
| A23L 5/20 | (2016.01) |
| A23P 10/40 | (2016.01) |
| A23L 3/36 | (2006.01) |
| B01D 11/02 | (2006.01) |
| B01D 1/22 | (2006.01) |
| B01D 1/18 | (2006.01) |

(52) U.S. Cl.
CPC .............. *A61K 36/185* (2013.01); *A23L 3/36* (2013.01); *A23L 3/46* (2013.01); *A23L 5/21* (2016.08); *A23L 5/23* (2016.08); *A23L 33/105* (2016.08); *A23P 10/40* (2016.08); *A61K 9/107* (2013.01); *B01D 1/18* (2013.01); *B01D 1/222* (2013.01); *B01D 11/0203* (2013.01); *B01D 11/028* (2013.01); *A23V 2002/00* (2013.01); *A61K 2236/39* (2013.01); *A61K 2236/53* (2013.01); *A61K 2236/55* (2013.01)

(58) Field of Classification Search
None
See application file for complete search history.

(56) References Cited

U.S. PATENT DOCUMENTS

| | | |
|---|---|---|
| 10,336,978 B2 | 7/2019 | Peet et al. |
| 2019/0231737 A1 | 8/2019 | Black et al. |

FOREIGN PATENT DOCUMENTS

| | | | |
|---|---|---|---|
| CA | 2235514 A1 | * | 5/1997 |
| WO | 2009090249 A1 | | 7/2009 |
| WO | 2015068052 A2 | | 5/2015 |
| WO | 2020168073 A1 | | 8/2020 |
| WO | 2021055777 A1 | | 3/2021 |

OTHER PUBLICATIONS

Mujumder et al. Some Innovative Drying Technologies for Dehydration of Foods, pp. 1-12, 2011. entire document, especially abstract, Table 1, p. 8, para 2.

* cited by examiner

*Primary Examiner* — Michael V Meller
(74) *Attorney, Agent, or Firm* — Seyfarth Shaw LLP; Brian Michaelis

(57) ABSTRACT

A powdered, water-soluble Full Spectrum Hemp Oil is formed using organic materials and natural products to form a non-GMO, fast acting, whole plant hemp extract without harsh chemicals such as hexane. The Full Spectrum Hemp Oil may be extracted using $CO_2$ concurrent gas extraction to avoid use of chemical additives.

11 Claims, 7 Drawing Sheets

PROCESS FOR MAKING A WATER SOLUBLE, FULL SPECTRUM HEMP OIL

CROSS-REFERENCE TO RELATED APPLICATION DATA

This application claims priority from U.S. Provisional Patent Application No. 62/986,901 filed Mar. 9, 2020 the contents of which are incorporated herein in their entirety, by reference.

TECHNICAL FIELD

The present application relates to processing organic materials.

BACKGROUND

The use of Cannibidiol (CBD) as a health supplement is increasingly widespread in today's market. Previous methods have focused on isolating specific strains of CBD in stable liposomal and micellar compositions, such as those in U.S. Patent Application Publication No. 2017/0279073. Additional methods have sought to isolate CBD in a particle sized for use in inhalants, such as in U.S. Pat. No. 10,328, 216. Such processes generally involve processing organic materials with complex chemical additives to create complex compounds and formulations

SUMMARY

Full Spectrum Hemp Oil product, according to the disclosure, may be suitable for use in foods, oils, inhalants, salves, cosmetics, and medicaments. The present disclosure provides an improved method for extracting a Full Spectrum Hemp Oil to form a food grade plant extract in powder form using organic materials.

According to the disclosure, raw, pre-processed cannabis source materials and biomass are subject to processes of: extraction to provide Full Spectrum extract; emulsion formulation to yield Full Spectrum Hemp Oil in an organic solution; and drying to provide a powder Full Spectrum Hemp Oil with a water content below 2%, a water activity below 1%, and 1% or less free fat to reduce loss of shelf-life due to rancid fats. The Full Spectrum Hemp Oil according to the disclosure has a high water solubility, and is the form of an organic, gluten-free end-product. The Full Spectrum Hemp Oil is dried to produce a powder with a D90 micron weight under 200 mg wherein approximately 90% of the particles are below approximately 200 micron. To control quality of the product, a hemp material may be tested for moisture content prior to forming the emulsion. The hemp material is ground to ensure substantially equal sizing of the material, thereby maximizing extraction of the desired Full Spectrum Hemp Oil from the source material. As a result, the Full Spectrum Hemp Oil product has a high, natural, shelf life without the use of chemical preservatives or chemical additives.

In an embodiment, the Full Spectrum Hemp Oil is extracted from the source material using $CO_2$ or ethanol extraction. The $CO_2$ gas extraction may utilize concurrent gas extraction. A $CO_2$ gas is directed concurrent to the source material. $CO_2$ gas extraction may be accomplished using a Supercritical Gas extractor such as the SCFN-P51 from Separeco Srl. The Full Spectrum Hemp extract may be diluted using an ethanol mixture. In an embodiment, the extract may be frozen as a part of the dilution process. The extract solution may pass through a filter at least once to remove any remaining source material from the solution. The solution may further pass through an ionized still or rotary evaporator to form a full spectrum product.

In a further embodiment, following extraction, the full spectrum product or extract solution may be used to form an emulsion. The extract solution or full spectrum product may be added to or combined with an emulsifying agent. A flow agent, such as gluten free, organic tapioca maltodextrine, may be used to enhance the process using natural ingredients. The resulting emulsifying solution is blended under high shear forces. In an embodiment of the disclosure, the emulsion may be dried into a powder using vacuum, spray drying or pulse spray drying techniques.

In a further embodiment, the extract or emulsion may be winterized by placing in a freezer for at least 24 hours. The extract or emulsion may then be filtered and polished. During polishing, a silica and ethanol mixture is heated. The extract or emulsion may be filtered through carbon materials as well as the silica and ethanol mixture. A vacuum may be applied to the filtration. The polished emulsion material may then be stored for powder creation.

According to the disclosure, an embodiment of a vacuum drying technique may include placing the extract or emulsion under a vacuum, stirring and heating the compound, and modulating the vacuum throughout the process to remove the ethanol mixture.

In another embodiment, a pulse spray drying technique may include accelerating combustion gases to a high speed and pumping the emulsion into the hot gas stream at low pressure and velocity. The high velocity pulse wave generated by the hot combustion gases atomizes and dries the emulsion into a powder. The combustion gases may be accelerated to at least 300 miles per hours (mph). The emulsion may be sprayed into the gas stream flow using a nozzle such as an open atomizer nozzle. The sprayed product may be at a low pressure and velocity, such as 1 psi. The powder may be formed in 1 second or less.

In an embodiment, the pulse spray drying technique may use a continuous/perpetual flow of the heated gas or a pulse flow of the heated gas. In the perpetual flow, the emulsion is introduced to the heated gas flow continuously. In the pulse flow, the emulsion is introduce in sequence with the generated pulses. The high speed drying of the emulsion product allows for reduced shear, increased particle size control, and retention of the product's natural characteristics. These natural characteristics may include concentration, taste, smell, nutritional value, etc.

Alternatively, conventional spray drying techniques may be implemented to transform the emulsion into a powder according to the disclosure. For example, the emulsion may be sprayed into a hot-air chamber to evaporate the liquid fraction, e.g., organic solvent or water, in the emulsion. As a function of the spray drying process a consistent particle size distribution may generally be obtained.

The resulting powder and/or emulsion may be 42% total dry weight Full Spectrum Hemp Oil. An exemplary powder and/or emulsion composition is 30% gum, 30% flow agent such as gluten free tapioca, and 40% dosed Full Spectrum Hemp or nutritional lipid emulsion containing Medium Chain Trigliceride oil. The product may include natural flavorings of coconut, coconut lemonade, and/or coconut hibiscus.

Full spectrum Hemp Oil preferably does not include harsh chemicals such as hexane unlike CBD isolate. The Full Spectrum Hemp Oil may include cannabinoids, terpenoids, and flavanoids.

The above summary has outlined, rather broadly, some features and advantages of the present disclosure in order that the detailed description that follows may be better understood. Additional features and advantages of the disclosure will be described below. It should be appreciated by those skilled in the art that this disclosure may be readily utilized as a basis for modifying or designing other structures for carrying out the same purposes of the present disclosure. It should also be realized by those skilled in the art that such equivalent constructions do not depart from the teachings of the disclosure as set forth in the appended claims. The novel features, which are believed to be characteristic of the disclosure, both as to its organization and method of operation, together with further objects and advantages, will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding of the present disclosure, reference is now made to the following description taken in conjunction with the accompanying drawings.

DETAILED DESCRIPTION

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. It will be apparent to those skilled in the art, however, that these concepts may be practiced without these specific details, and/or that the order of steps shown in flow diagram form may be altered or otherwise modified and implemented in steps to achieve the disclosed concepts.

The present disclosure provides a process or method of manufacturing a Full Spectrum Hemp Oil product suitable for use in foods, oils, inhalants, salves, cosmetics, medicaments, among other products. The Full Spectrum Hemp Oil according to the disclosure is produced with a water content preferably below 2%, a water activity below 1%, and 1% or less free fat to reduce loss of shelf-life due to rancid fats.

The Full Spectrum Hemp Oil is derived from an emulsion of hemp material using a drying process such as pulse spray drying. The pulse spray drying process accelerates combustion gases to a high speed and pumps an emulsion into the heated gas stream at low pressure and velocity. A high velocity pulse wave generated by the heated combustion gases atomizes and dries the emulsion into a powder.

Figure 1:
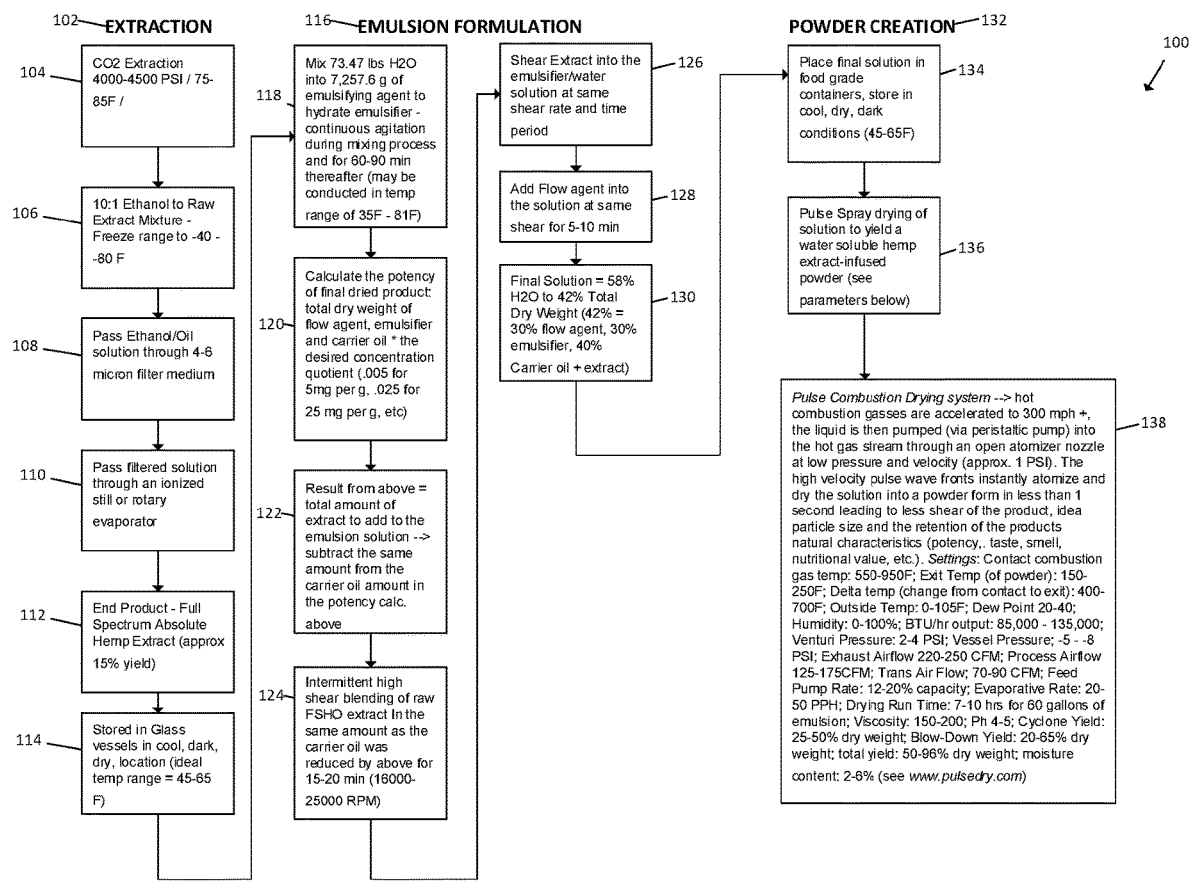
FIG. 1 illustrates a flow diagram of an embodiment of a process of forming a powdered emulsion according to the disclosure.
Figure 2:
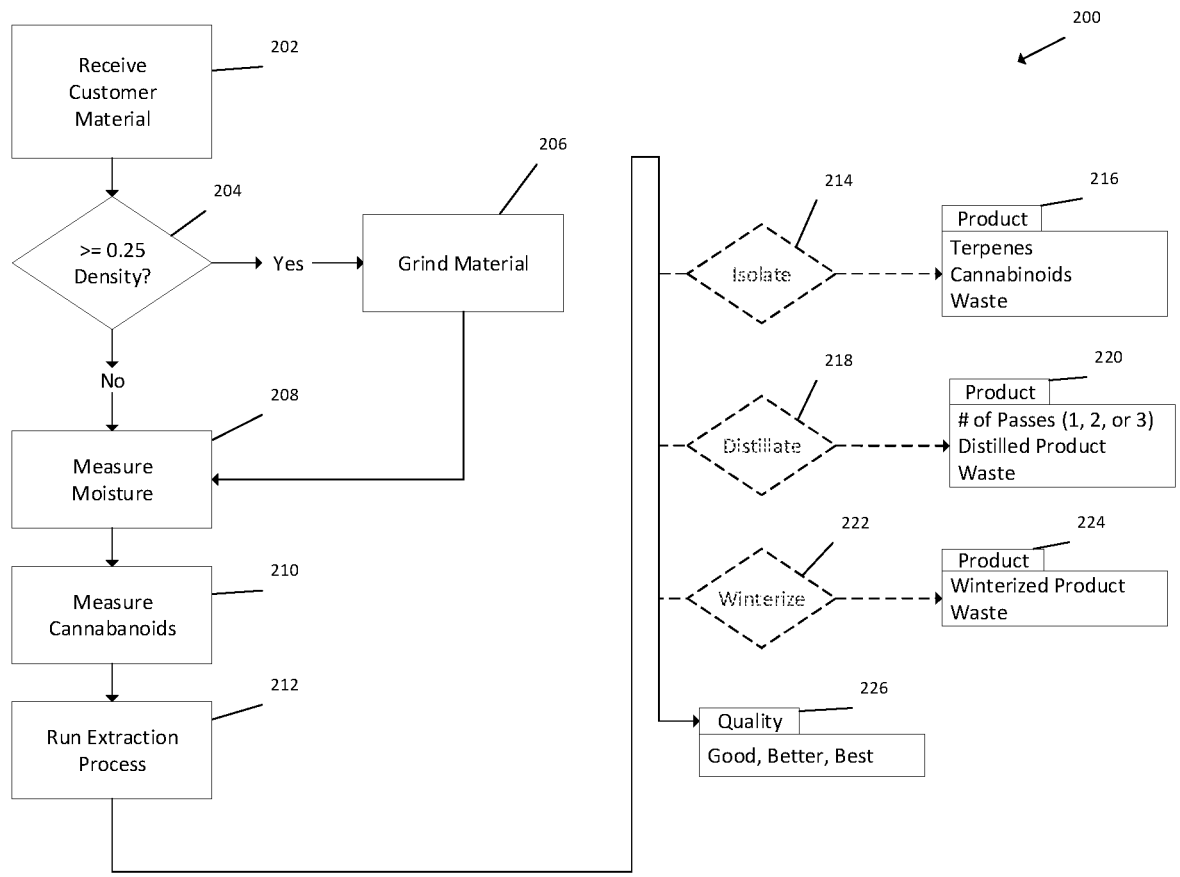
FIG. 2 illustrates a flow diagram of an embodiment of a process of extraction according to the disclosure.

FIG. 1 illustrates a flow diagram of an embodiment of a process or method for forming a powdered emulsion according to the disclosure. In an extraction phase 102, the Full Spectrum Hemp Oil is extracted from the source material using CO2 extraction 104, however, it should be appreciated that alternative extraction solvents may be implemented, such as ethanol extraction. The CO2 gas extraction 104 may utilize concurrent gas extraction. A CO2 gas is directed concurrent to the source material. CO2 gas extraction 104 may be accomplished using a Supercritical Gas extractor such as the SCFN-P51 from Separeco Srl. In the CO2 extraction 104, the raw, pre-processed cannabis source material or biomaterial may be processed using CO2 gas extraction at a range of around 75-85 degrees Fahrenheit. The CO2 gas may be at a pressure of around 4000-4500 PSI.

The Full Spectrum Hemp extract may be diluted 106 using a solvent such as an ethanol mixture to form an extract solution. In an embodiment, the extract solution may be frozen as a part of the dilution process in a step known as winterization discussed in greater detail hereinafter. The extract solution may pass through a filter 108, such as a 4-6 micron filter medium, at least once to remove any remaining source material from the extract solution. The filtered extract solution may further pass through an ionized still or rotary evaporator 110 to form a full spectrum filtered extract 112. The solution may be processed at conditions around 77 degrees Fahrenheit and 1.38 PSI to 86 degrees Fahrenheit and 1.78 PSI. The Full Spectrum Hemp Oil filtered extract derived from the extraction may be a yield of approximately 11-15% of the biomass 112. For example, a raw biomass of 100 lbs may produce around 11-15 lbs of extract. A person of ordinary skill in the art should appreciate that a higher quality raw biomass may result in an increased yield of extract and similarly, a lower quality may result in a decreased yield.

The full spectrum filtered extract 112 may be stored in glass vessels for later processing 114. If stored, such storage should be in a cold, dark, dry location at a temperature range of approximately 45-65 degrees Fahrenheit.

Alternatively, as further illustrated in FIG. 1, the full spectrum filtered extract 112 may be further processed right after the extraction process 102 is completed. Once the Full Spectrum Absolute Hemp filtered extract is derived (112) it may be further processed in an emulsion formulation phase 116 to form an emulsion. A solvent such as water may be mixed with an emulsifying agent to form an emulsion solution 118. For example, 73.47 lbs. H2O may be added to 7,257.6 grams of emulsifying agent to form the emulsion solution 118. The emulsion solution 118 may be subjected to agitation during a mixing process, that may, for example, be conducted for 60-90 minutes at a temperature in a range of around 35 F to 80 F to provide a substantially uniform emulsion solution.

A carrier oil may also be added 120. The desired potency of the final dried product is used to calculate how much Full spectrum Hemp Oil extract to add to the emulsion solution. An exemplary equation is described below:

Total dry weight=dry weight of flow agent+emulsifier+carrier oil$_{initial}$.

Amount of extract to add to emulsion solution=total dry weight×desired concentration quotient.

For example, the desired concentration quotient may be 0.005 for 5 mg per gram or 0.025 for 25 mg per gram. If the total dry weight=100 grams and the desired concentration is 1 mg/g, the resulting amount may be 100 mg (or 0.1 g).

The resulting amount 122 is approximately the amount of Full Spectrum Hemp Oil extract to be added to the emulsion solution. The same amount, i.e., amount of Full Spectrum Hemp Oil extract, is subtracted from the carrier oil amount 122 to avoid changing the total dry weight. In other words:

Amount of carrier oil to be added=carrier oil$_{initial}$−amount of extract to be added to emulsion solution.

The raw Full Spectrum Hemp Oil extract may be subjected to intermittent high shear blending 124. For example, the high shear blending may be conducted for around 15-20 minutes at around 16000-25000 RPM. The shear extract may then be added to the emulsion solution and mixed 126 at about the same rate and for the same time period. Mixing may occur under intermittent high shear blending. A flow agent may be added 128 to the solution, also under intermittent high shear blending, and the resulting mixture blended for around 5-10 minutes. The flow agent may include gluten free, organic, tapioca maltodextrine. The flow agent may advantageously enhance the process using natural ingredients.

The final solution, i.e., resulting emulsion, may be approximately 58% H20 to 42% total dry weight 130. The total dry weight may include a ratio of around 30% flow agent, 30% emulsifier, and 40% carrier oil+extract.

The resulting emulsion may be subject to a powder creation phase 132, as described hereinafter, or it may be stored 134. If stored, the resulting emulsion may be stored in food grade containers, in cool, dry, dark conditions, at around 45-65 degrees Fahrenheit. In the powder creation phase 132, the resulting emulsion is powderized to achieve the final product. In one embodiment, for example, pulse spray drying may be used to convert the resulting emulsion into a powder, although it should be appreciated by those skilled in the art that other drying approaches for powderization may be implemented according to the disclosure.

As further illustrated in FIG. 1, drying is implemented to yield powderized product that is optimally a water soluble hemp extract-infused powder 136. In an exemplary embodiment, pulse combustion drying is used to form the powder 138. The pulse combustion drying may include accelerating combustion gases to at least 300 miles per hour. The resulting emulsion from the emulsion formulation phase may be pumped, using for example a peristaltic pump, into the hot gas stream. An open atomizer nozzle may be used to inject the resulting emulsion solution into the combustion gases. The emulsion enters the heated gas stream at a low pressure and velocity, such as around 1 PSI or below and 1 ft/s or below. The high velocity pulse wave fronts instantly atomize and dry the solution into a powder form in less than 1-3 seconds leading to less shear of the powdered product, ideal particle size and the retention of the products natural characteristics (potency, taste, smell, nutritional value, etc.).

An illustrative pulse combustion drying process for the powder creation phase 132 according to the disclosure, may be implemented using a pulse combustion drying system such as available from Pulse Combustion Systems of Payson, Ariz. 85541 (see www.pulsedry.com).

In an illustrative drying process to form the powder 138, contact combustion gas temperature may be approximately 550-950 F, and exit temperature of the powder may be approximately 150-250 F, indicating a change from contact to exit temperature (DeltaTemp) of approximately 400-700 F. The illustrative drying process may be implemented at an ambient/outside temperature of approximately 0-150 F, with a dew point of 20-40 F and humidity of 0-100%. Some illustrative operating parameters of a pulse combustion system dryer implemented for the powder creation phase 132, include; BTU/hr Output of approximately 85,000-135,000; Venturi Pressure of approximately 2-4 PSI; Vessel Pressure of approximately −5−−8 PSI; Exhaust Airflow of approximately 220-250 CFM; Process Airflow of approximately 125-175 CFM; Transfer Airflow of approximately 70-90 CFM; Feed Pump Rate of approximately 12-20% capacity; Evaporative Rate of approximately 20-50 PPH; Drying Run Time of approximately 7-10 hrs for 60 gallons of emulsion; Viscosity of approximately 150-200; Ph of approximately 4-5; Cyclone Yield of approximately 25-50% dry weight; Blow-Down Yield of approximately 20-65% dry weight; Total Yield of approximately 50-96% dry weight; and Moisture Content of approximately 2-6%.

The formation of the powder may take a second or less to limit shear of the product. Accordingly, the particle size and retention of the product's natural characteristics may be controlled. Natural characteristics of the end-product that may benefit from pulse combustion drying in the powder creation phase 132, include, but are not limited to, potency, taste, smell, and nutritional value. The powder's particles may be controlled such that approximately 90% of the particles are below 200 micron. The particles are preferably a generally consistent size throughout the powder.

Although a high velocity pulse wave may be generated to allow the emulsion to be added in sequence with the generated pulses, and atomize and dry the emulsion into a powder, it should be appreciated that a continuous/perpetual flow may be used. The perpetual flow may allow continuous introduction of the emulsion to the heated gas flow.

Similarly, in an alternative implementation, a conventional spray drying technique may be implemented to derive the powder from the emulsion according to the disclosure. For example, the emulsion may be sprayed into a hot-air chamber to evaporate the liquid fraction, e.g., organic solvent or water in the emulsion. As a function of the spray drying process a consistent particle size distribution may generally be obtained.

FIG. 2 illustrates a flow diagram of an embodiment of a method or process of cannabis extraction 200 according to the disclosure. The biomaterial is received 202 from a source such as a customer desiring conversion of marijuana biomass into a powder, e.g., for use in making edibles, drinks, salves, medicaments, and/or other consumable items. The biomaterial is measured 204 to determine its density. If the biomaterial greater than a density of 0.25 or is in a form or shape unsuitable for processing, the biomaterial may be ground 206, such as by mechanical grinding.

As part of the grinding process 206, the biomaterial may be checked for foreign material such as non-cannabis leaves, wrappers, plastic, and metal objects. Ideally, only biomaterial such as cannabis buds and leaves are ground 206. The biomaterial is loaded into a tool for grinding and checked to ensure the biomaterial is properly placed. For example, that there are no large voids in the material and the material is not tightly packed. As a result of the grinding process 206, the biomaterial should occupy a reduced volume, indicated by a reduced height, but maintain a similar weight to the preground weight. For example, the biomaterial may be within 20-50 grams of the original weight. The weight may be different depending on the amount and type of foreign material removed.

The biomaterial may be checked for moisture content 208. A tool such as the Intelligent-Lab™ Moisture Analysis Balance, Model: DSH-50-10 may be used, or any other device capable of measuring a moisture content in a biomaterial. To measure the moisture content 208, the device is set to pre-measuring parameters. This may include turning the device on and allowing it to warm up for at least 30 minutes depending on the model used. For example, the DSH-50-10 may use the parameters of Temperature: 100 degrees Celsius and Time: Auto. A predetermined amount of the biomaterial, such as 1 gram, is placed in the device for measuring the moisture content 208.

The biomaterial's cannabinoid content may be measured 210. The cannabinoid content may be measured as % CBD and/or % Total Active Cannabinoids (TAC). The CBD is preferably at least 50%. A high quality biomaterial may yield a measurement of 65-70% CBD. Other cannabinoids in the biomaterial may be at least 3% depending on the quality of the biomaterial. The TAC is preferably at least 53%. A person of ordinary skill in the art should appreciate the % cannabinoid content may be higher or lower depending on the biomass without deviating from the scope of the disclosure.

If the biomaterial is measured to be at acceptable parameters, the biomaterial is run through the extraction process 212 (described in further detail in relation to FIG. 1), to obtain a Full Spectrum Absolute Hemp extract. The yield may be approximately 11-15%. For example, 100 grams of biomaterial may yield 15 grams of Full Spectrum Absolute Hemp extract depending on the quality of the biomaterial.

Because the process disclosed herein is a Full Spectrum process, no additives or synthetic chemicals are used. As a result, the quality of the finished product depends on the quality of the raw biomaterial used. A higher quality biomaterial will yield a higher quality product. Additionally, a higher quality biomaterial may produce a higher yield of extract.

Optionally, the extract may be processed by at least one of isolation/isolated 214, distillation/distillated 218, and/or winterization/winterized 222 processes, or none of the above depending on the desired product. An isolation process 214 may be conducted using chromatography, such as High Performance Liquid Chromatography (HPLC). For example, a crude extract may be run through a chromatography machine having a vessel with water or ethanol and a very fine silica sand. The extract may be added to the vessel and, using temperature and pressure, each part of the extract can be isolated separately 216. For example, a desired temperature and pressure may be used to isolate the terpenes in the extract, or a different temperature and pressure may be used to isolate the cannabinoids, flavonoids, etc. The isolate product may be around 96-99% pure TAC which includes CBD. Isolation 214 may be used to remove THC from the extract.

A distillation process 218 including one or more passes may be completed resulting in a distilled product and a waste product. During distillation 218, the extract may be washed with ethanol and placed in a vacuum to vaporize certain volatiles out, such as terpenes, e.g., to make a more potent distilled product. The extract may be distilled 218 one or more times to increase the potency of the product. The distilled product 220 may be around 80-85% TAC. As a result of the distillation process 218, the distilled product 220 may lack flavonoids, terpenes, and/or active cannabinoids as a function of what is to be distilled off the extract.

In addition or as an alternative to isolation 214 and/or distillation 218 processes, a winterization process 222, producing a winterized product 224 and a waste product, may be completed as described hereinafter with reference to FIGS. 4A, 4B, and 5.

The extract may be tested 226 to determine the quality of the product to categorize same, for example as "good," "better," or "best."

Figure 3:
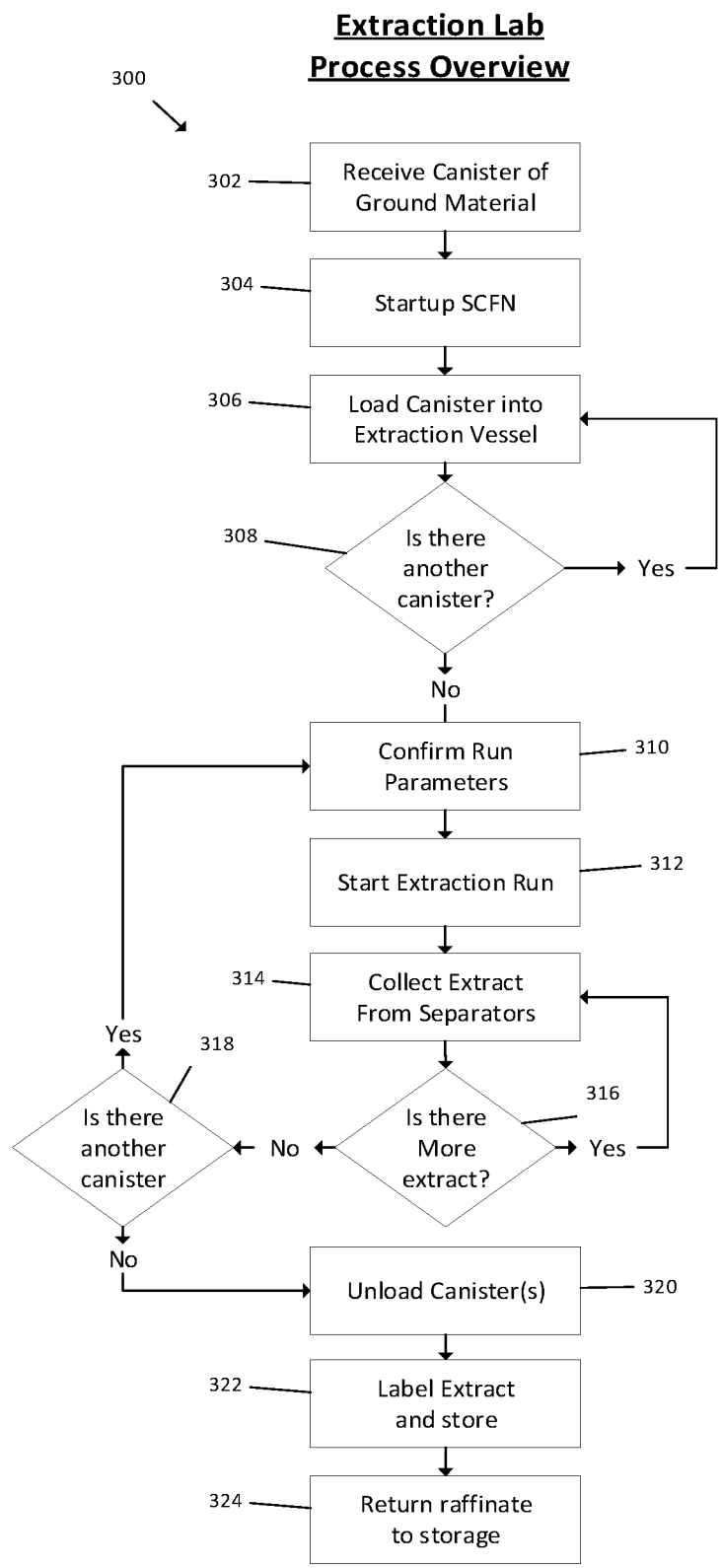
FIG. 3 illustrates a flow diagram of a further embodiment of a process of extraction according to the disclosure.

FIG. 3 illustrates an overview flow diagram of further processing involved in the extraction phase (102, FIG. 1) according to the disclosure. In the extraction processing 300, CO2 gas extraction may be used to extract a desired Full Spectrum Absolute Hemp extract, for example, using a Supercritical Gas extractor such as the SCFN-P51 from Separeco Srl. The biomaterial may be prepared in a vessel such as an extraction canister 302. Following startup/confirming the extractor is ready 304, the biomaterial may be loaded into the extraction vessel 306. If there are multiple extraction canisters of biomaterial 308, each may be loaded into the extraction vessel 306.

The extraction parameters are set/confirmed 310 and the extraction is run on the biomaterial 312. Following the run, the extract is collected from the separators 314. If more extract remains 316, collection may continue until all the extract is collected. If additional extraction is required, such as if there are additional extraction canisters 318, additional extraction runs 312 may be conducted.

The extraction canisters containing the biomaterial extract are unloaded 320. The biomaterial extract may be labeled and stored 322. Raffinate, the remaining biomaterial, may be returned to storage 324 or otherwise disposed of.

Figure 4A:
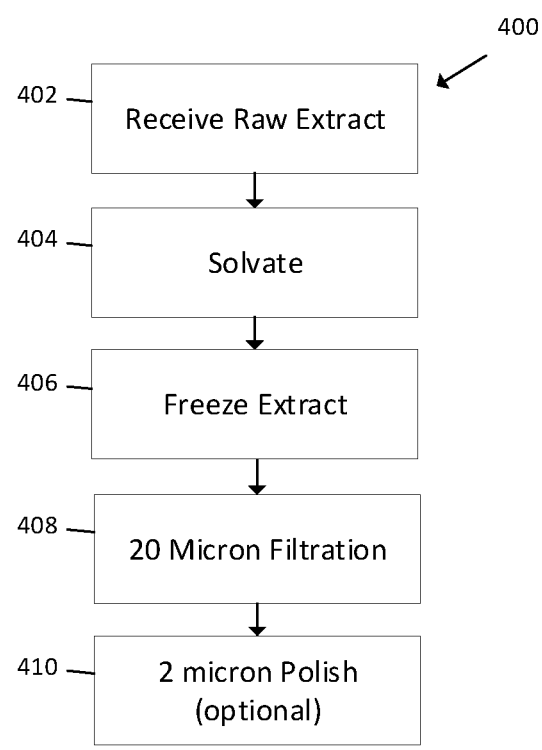
FIG. 4A illustrates a flow diagram of an embodiment of a winterization process according to the disclosure.

FIG. 4A illustrates a flow diagram of an embodiment of a winterization process 400 according to the disclosure. The winterization process 400 is an optional step in the extraction process, wherein raw extract of biomaterial may be received 402, such as from the SCFN extractor. The raw extract may be solvated 404. Solvation is accomplished by heating and dissolving the raw extract in a solvent such as ethanol. For example, a water bath heated to around 140-145 degrees Fahrenheit may be used to melt the raw extract. If desired, the raw extract may be homogenized.

The raw extract may be combined with ethanol sufficient to produce an approximately 10:1 ratio of ethanol to extract, i.e., 10 parts ethanol to 1 part extract. The ethanol may be heated and combined with the melted raw extract. The melted raw extract and ethanol are mixed. The heated mixture may be reheated and mixed until the melted raw extract is solvated. For example, the mixing may continue until homogenized and the melted raw extract is completely solvated to produce a solvated extract.

The mixture may be cooled and placed in a freezer 406 for a predetermined length of time until winterized. For example, the mixture may be placed in the freezer for at least 24 hours. The freezer may be within a temperature range of about −40 to −80 degrees Fahrenheit. The winterized extract may be placed in a container such as a Buchner funnel before filtration 408. Filtration of the winterized extract may include using a 20 micron filter medium/paper to produce a filtrate, i.e., a filtered extract.

The filtration process may use vacuum filtration by applying a vacuum to draw the extract through the filter. The filtered extract may be polished 410 if desired. Polishing the extract may include further filtering the extract using a 1-2 micron filter. A silica-ethanol mixture may be added to the filtered extract to prepare the extract for polishing. For example, 175 grams of silica and 500 grams of ethanol may be mixed and added to the filtered extract. A vacuum may be applied to draw the extract through the filter. In an alternative embodiment, the extract may be pushed through the filter. The polishing 410 produces an absolute, i.e., a polished, extract. The polished extract may have a concentration below 500 ppm.

Figure 4B:
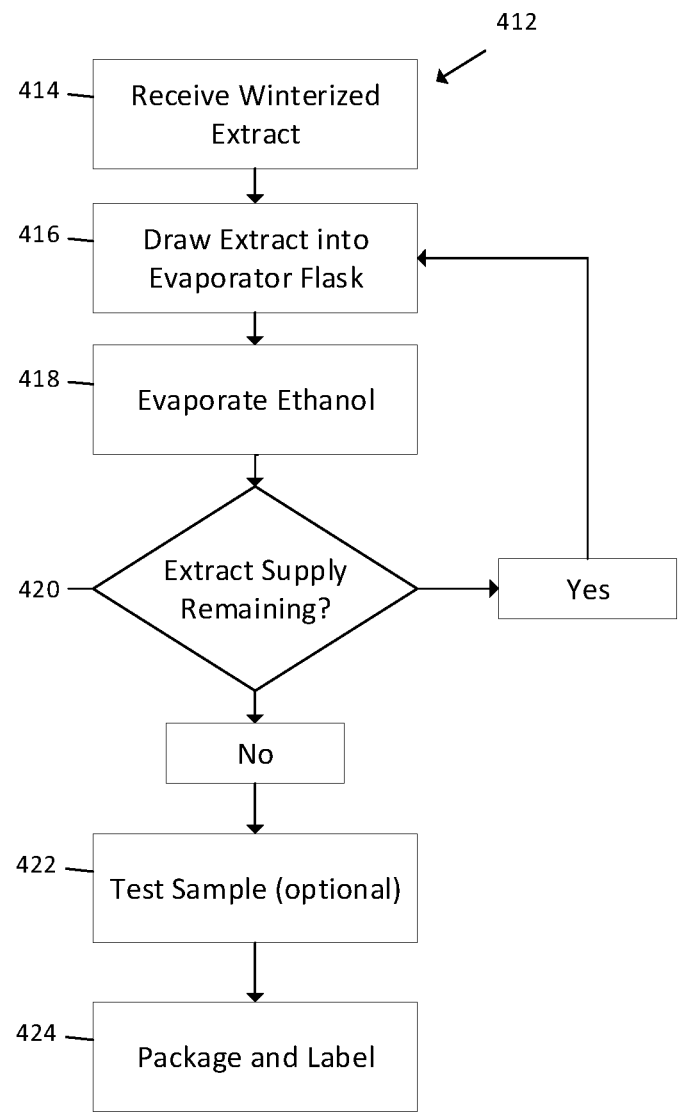
FIG. 4B illustrates a flow diagram of an embodiment of an evaporation process according to the disclosure.

FIG. 4B illustrates a flow diagram of an embodiment of an evaporation process 412 according to the disclosure. The winterized or polished extract may contain a solvent such as ethanol. To remove the solvent, an evaporation process 412 may be completed. The winterized or polished extract 414 may be drawn into a container such as an evaporator flask 416. The solvent, in this example ethanol, may be heated to evaporate 418 the solvent. Some or all of the solvent may be reclaimed as part of the evaporation process.

If additional winterized or polished extract 414 requires evaporation, the process may be repeated 420. The extract may be tested 422 to ensure the quality of the extract following evaporation. The extract may be packaged and labeled for storage 424.

Figure 5:
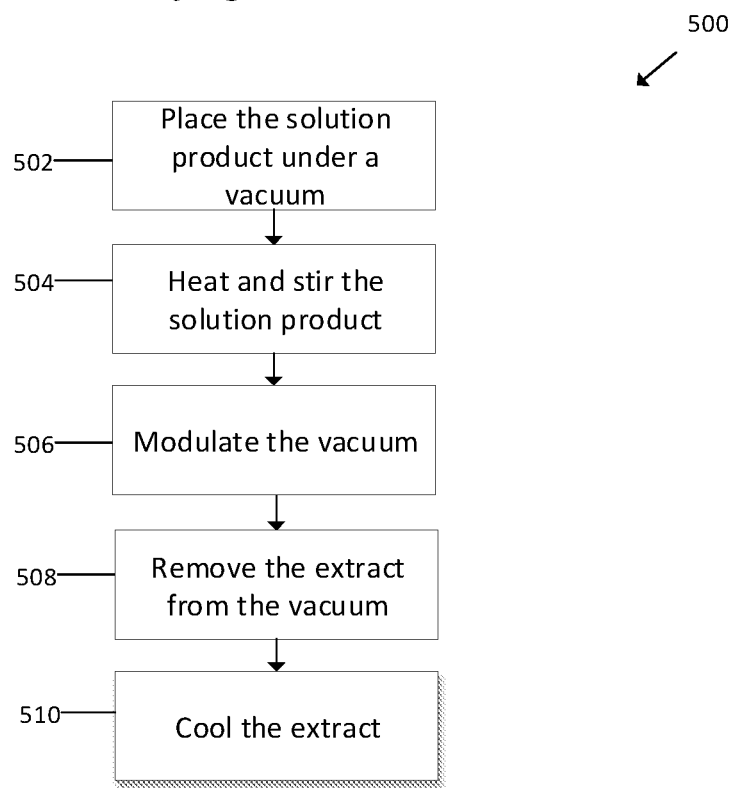
FIG. 5 illustrates a flow diagram of an embodiment of a vacuum drying process according to the disclosure.

FIG. 5 illustrates a flow diagram of an embodiment of a vacuum drying process 500 according to the disclosure. The vacuum drying process 500 may be used as an alternative to the pulse spray drying process described hereinbefore with reference to FIG. 1, and further illustrated in FIG. 6. The vacuum drying process 500 may include placing a solution product such as the winterized/polished extract under a vacuum 502. The solution product may be heated and stirred 504 while under the vacuum to draw out and evaporate the solvent.

For example, the solution product may be stirred at a rate of around 30-50 rpm to achieve agitation. In an embodiment of the vacuum drying process 500, the solution product may be heated in a range of around 35 degrees Celsius at 100 mm/Hg to around 55 degrees Celsius at 255 mm/Hg to achieve evaporation of the solvent. The solution product should not be heated to above 90 degrees Celsius.

The vacuum is modulated 506 to complete evaporation and return the solution product to environmental/atmospheric pressure. For example, the vacuum may be modulated between a high vacuum pressure such as those described above and atmospheric pressure. The solution product is cooled 510 to complete the vacuum drying process 500. The solution product may be removed while at a temperature of around 60-80 degrees Celsius due to its advantageously low viscosity.

Figure 6:
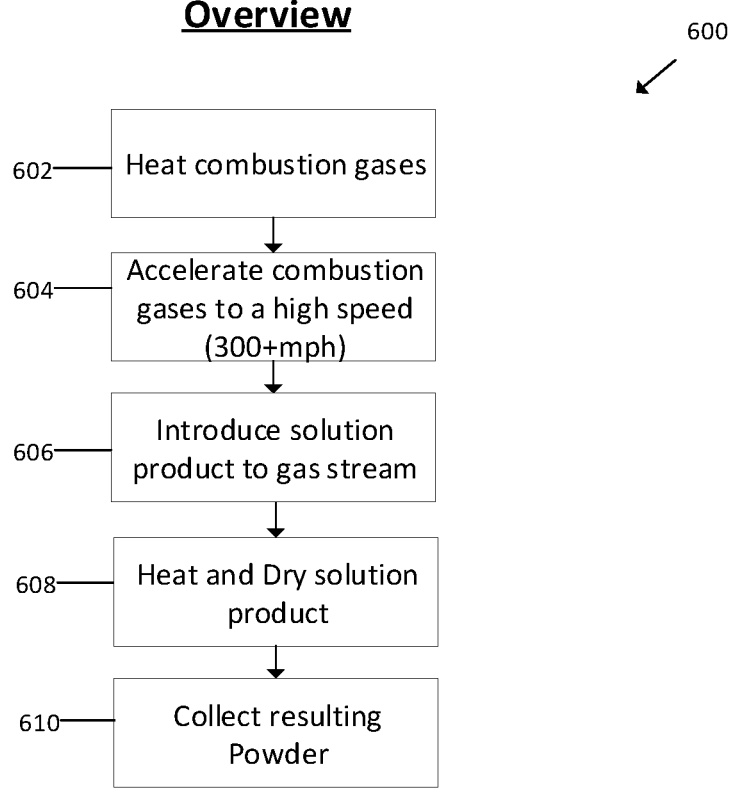
FIG. 6 illustrates a flow diagram of an embodiment of a pulse combustion drying process according to the disclosure.

FIG. 6 illustrates an overview flow diagram of an embodiment of a pulse combustion drying process 600 according to the disclosure (and as described hereinbefore with respect to FIG. 1). Combustion gases are heated 602 and accelerated 604. The combustion gases may be accelerated to at least 300 miles per hour. The emulsion may be injected into the gas stream 606. The product is then heated and dried 608. The resulting powder is collected 610.

The powdered Full Spectrum Hemp Oil is water soluble and can be used as a dry powder or rehydrated. The powder may have a D90 micron weight under 200 mg wherein approximately 90% of the particles are below 200 micron. The powder and/or emulsion may be 42% total dry weight Full Spectrum Hemp Oil. An exemplary powder and/or emulsion composition is 30% gum, 30% flow agent such as gluten free tapioca, and 40% dosed Full Spectrum Hemp or nutritional lipid emulsion containing Medium Chain Trigliceride oil. The product may include natural flavorings such as coconut, coconut lemonade, and/or coconut hibiscus. The flavoring may result from the use of natural ingredients such as organic tapioca maltodextrine.

The powder may be non-psychoactive, i.e. THC content is <0.3%, and non-GMO.

The powder may be used in cooking processes such as baking. The powder may be mixed into drinks and preferably has a high bioavailability. Advantageously, the generally consistent particle size allows for a consistent dosage and effect. The powder may include electrolytes and other nutrients that promote hydration and recovery. The powder may also be used to make medicaments such as salves and/or massage oil.

An exemplary salve, provided by way of example only, may include organic calendula flowers infused in extra virgin olive oil (16 oz) and/or organic St. Johnswort flowers infused in extra virgin olive oil (16 oz), pure beeswax beads (14 oz), organic lavender essential oil (0.1 oz), organic lemongrass E O (0.1 oz), Organic peppermint E O (0.1 oz), and hemp extract (9600 mg for a 2 oz container). The carrier oils may be heated to 150 degrees Fahrenheit before adding the beeswax. The hemp extract is added and mixed until fully incorporated. The solution may be removed from heat and the essential oils mixed. The ingredients and their amounts may be changed as desired without departing from the disclosure, i.e., some or all of the above ingredients may be used or substituted as needed.

An exemplary massage oil, provided by way of example only, may include full spectrum extract (28.5 grams) mixed with sweet almond oil (112 oz), grape seed oil (112 oz), rose essential oil (1 oz), and/or lavender essential oil (1 oz). The mixture is blended until fully mixed, i.e., homogenous. Clary sage (0.6 oz), ylang ylang (1 oz), and or vitamin E (0.1 oz) may also be added. The mixture may be further blended to incorporate the additions. The ingredients and their amounts may be changed as desired without departing from the disclosure, i.e., some or all of the above ingredients may be used or substituted as needed.

It should be understood that other embodiments may be realized and that logical and physical changes may be made without departing from the spirit and scope of the disclosure. Thus, the detailed description herein is presented for purposes of illustration only and not of limitation. For example, the steps recited in any of the method or process descriptions may be executed in an order other than as presented and are not limited to the order presented. Moreover, references to a singular embodiment may include plural embodiments, and references to more than one component may include a singular embodiment.

The description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein but is to be accorded the widest scope consistent with the principles and novel features disclosed herein, and is envisioned as encompassing the scope described in the appended claims and the full range of equivalents of the appended claims.

What is claimed is:

1. A method of forming a Full Spectrum Hemp Oil powder consisting essentially of:
   a) providing hemp;
   b) extracting the hemp with CO2 gas extraction to yield a hemp extract;
   c) winterizing the hemp extract;
   d) filtering the hemp extract mixture with either an ionized still or a rotary evaporator to obtain a filtered hemp extract;

e) forming an emulsion solution by mixing the filtered hemp extract with maltodextrin to yield the emulsion solution;

f) blending the emulsion solution using an intermittent high shear blending process to form an emulsion; and g) spray drying the emulsion using a pulse spray drying process to yield a Full Spectrum Hemp Oil powder.

2. The method of claim 1, wherein the spray drying is pulse spray drying and wherein during the spray drying, accelerating at least one combustion gas to at least 300 mph and spraying the emulsion into the accelerated combustion gas.

3. The method of claim 1, wherein the emulsion is spray dried using a pulse combustion process consisting essentially of accelerating at least one combustion gas, injecting the emulsion into a gas stream formed by the accelerated combustion gas, heating and drying the emulsion to form a powder and collecting the powder.

4. The method of claim 3, further consisting essentially of determining the density of the Full Spectrum Hemp Oil powder.

5. The method of claim 3, wherein the maltodextrin is organic tapioca maltodextrin.

6. The method of claim 3, further consisting essentially of measuring the moisture content of the hemp, and measuring the cannabinoid content of the hemp.

7. The method of claim 3, further consisting essentially of performing distillation on the hemp.

8. The method of claim 3, wherein winterizing the hemp consists essentially of mixing the extract with a solvent in a ratio of 10 parts solvent to 1 part extract to form a mixture; heating the mixture until the extract is solvated; freezing the mixture for at least 24 hours at a temperature between −40 to −80 degrees Fahrenheit; and filtering the mixture.

9. The method of claim 1, wherein the intermittent high shear blending is blending the emulsion solution for at least 15 minutes at approximately 16000-25000 RPM.

10. The method of claim 1, wherein the emulsion solution is approximately 58% water to 42% total dry weight.

11. The method of claim 1, wherein the emulsion is dried using a continuous flow spray drying process.

* * * * *